US00PP14742P2

(12) United States Plant Patent
Olesen et al.

(10) Patent No.: US PP14,742 P2
(45) Date of Patent: Apr. 27, 2004

(54) MINIATURE ROSE VARIETY 'POULHI012'

(50) Latin Name: *Rosa hybrida*
Varietal Denomination: POULhi012

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/434,932

(22) Filed: May 9, 2003

(51) Int. Cl.[7] ..... A01H 5/00
(52) U.S. Cl. ..... Plt./117
(58) Field of Search ..... Plt./117

*Primary Examiner*—Bruce R. Campell
*Assistant Examiner*—Susan B. McCormick

(57) ABSTRACT

A new miniature rose which has abundant, near white flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE INVENTION

Classification:

Botanical: Rosa hybrida 'POULhi012'.

Commercial: Miniature.

The present invention constitutes a new and distinct variety of miniature rose plant which originated from a controlled crossing between Patricia Kordana, described and illustrated in U.S. Plant Pat. No. 11,242 issued on Feb. 22, 2000 and an unnamed seedling, non-patented. The two parents were crossed and the resulting seeds were planted in a controlled environment. The new variety is named 'POULhi012'.

The new rose may be distinguished from its seed parent, 'Patricia Kordana', by the following combination of characteristics:

1. 'Patricia Kordana' has a petal count of 25 to 30, while that of 'POULhi012' is 75 to 85.
2. The general tonality of 'Patricia Kordana' is Yellow-Orange Group 19D, while that of 'POULhi012' is Green-White Group 157C.
3. The thorn color of 'Patricia Kordana' is Greyed-Orange Group 177D, while that of 'POULhi012' is Greyed-Red Group 181D.

The new variety may be distinguished from its pollen parent, an unnamed created by the same inventors, by the following combination of characteristics:

1. The pollen parent has a general tonality of Orange-Red Group 35B, while that of 'POULhi012' is Green-White Group 157C.
2. The pollen parent has a petal count of 25, while that of 'POULhi012' is 75 to 85.

The objective of the hybridization of this rose variety for commercial culture was to create a new and distinct variety with unique qualities, such as:

1. Uniform and abundant flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type and distinguish 'POULhi012' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULhi012' was selected by the inventors as a single plant from the progeny of the hybridization in 1999.

Asexual reproduction of 'POULhi012' by cuttings and traditional budding was first done by L. Pernille and Mogens N. Olesen in their nursery in Fredensborg, Denmark in June of 2000. This initial and other subsequent propagations conducted in controlled environments have demonstrated that the characteristics of 'POULhi012' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULhi012'. Specifically illustrated in SHEET 1:

1. Stem showing branching and the attachment of leaves, buds, and peduncles;
2. Flower bud, partially opened bud, and open bloom;
3. Flower petals, detached;
4. Sepals, receptacle, and pedicel;
5. Stem as well as a bare stem exhibiting thorns;
6. Leaves.

DETAILED DESCRIPTION OF THE VARIETY

The following is a description of 'POULhi012', as observed in its growth in Half Moon Bay, Calif. Color references are made using The Royal Horticultural Society (London, England) Colour Chart, 1995, except where common terms of color are used.

For a comparison, several physical characteristics of the rose variety 'POULhi001', a rose variety from the same inventors described and illustrated in U.S. Plant Pat. No. 13,493 and issued on Jan 21, 2003 are compared to 'POULhi012' in Chart 1.

CHART 1

| | 'POULhi012' | 'POULhi001' |
|---|---|---|
| General tonality | Green-White Group 157C. | Yellow Group 13B. |
| Thorn color | Greyed-Red Group 181A. | Greyed-Orange Group 163A. |
| Petalage | 75 to 85. | 40 to 50. |

Parents: 'Patricia Kordana'×an unnamed seedling.

FLOWER AND FLOWER BUD

Blooming habit: Recurrent.

Flower bud:

*Size.*—Upon opening, 28 mm in length from base of receptacle to end of bud.

*Bud form.*—Short, pointed ovoid.

*Bud color.*—As sepals unfold, Yellow-Green Group 150D. At ¼ opening, Yellow-Green Group 150D.

*Sepals.*—Both upper and lower surfaces are Green Group 137B at margins and Yellow-Green Group 144D in interior. Weak foliaceous appendages on three of the five sepals. Surfaces of sepals slightly pubescent. Stipitate glands are scantily present on sepal edges. Shape: Sepal apex is cirrose. Base is flat at union with peduncle. Size: 25 mm long×6 mm wide.

*Receptacle.*—Surface: Smooth. Shape: Funnel-shaped. Size: 5 mm (h)×8 mm (w). Color: Yellow-Green Group 144A.

*Peduncle.*—Surface: Smooth. Length: 20 to 40 mm average length. Color: Green Group 138A. Strength: Upright.

*Borne.*—Singly.

*Anthocyanin.*—None observed.

Flower bloom:

*Fragrance.*—None.

*Duration.*—As a pot plant, flowers last from 8 to 10 days.

*Size.*—Medium for 12–15 cm pot rose. Average flower diameter is 55 mm when open.

*Form.*—Shape of flower when viewed from the side: Upon opening, upper part:Flat. Upon opening, lower part:Flat. Open flower, upper part: Flat. Open flower, lower part: Concave.

*Petalage.*—Average range: 75 to 85 petals under normal conditions with 5 to 7 petaloids.

Color:

*Upon opening, petals.*—Outermost petals: Outer Side: Green-White Group 157C. Inner Side: Green-White Group 157C. Innermost petals: Outer Side: Green-White Group 157C. Inner Side: Green-White Group 157C.

*Upon opening, basal petal spots.*—No distinctive coloration at petal base observed.

*After opening, petals.*—Outermost petals: Outer Side: Green-White Group 157C. Inner Side: Green-White Group 157C. Innermost petals: Outer Side: Green-White Group 157C. Inner Side: Green-White Group 157C.

*After opening, basal petal spots.*—No distinctive coloration at petal base observed.

General tonality: On open flower Green-White Group 157C. No change in the general tonality at the end of the 6th day. Afterwards, general tonality is Green-White Group 157C.

Petals:

*Petal reflex.*—Moderate.

*Petal edge.*—Entire, with notch in center of margin.

*Shape.*—Apex is Deltoid, base is acute.

*Petaloids.*—Quantity: 5 to 7. Size: 15 mm long; 7 mm wide. Color: Green-White Group 157C.

*Thickness.*—Thin.

*Arrangement.*—Formal.

Reproductive organs:

*Pistils.*—Length: 4 to 5 mm long. Quantity: 94.

*Pollen.*—Color: Yellow-Orange Group 14B. Quantity: Scant.

*Anthers.*—Size: 3 mm long. Color: Yellow Group 13A. Quantity: 56.

*Filaments.*—Color: Yellow Group 8D. Length: 1 to 3 mm.

*Stigmas.*—Slightly superior in location to anthers. Color: Yellow Group 4D.

*Styles.*—Color: Yellow Group 4D.

*Seed formation.*—No hips observed.

PLANT

Plant growth: Vigorous, compact, and upright. When grown as a 12–15 cm pot plant, the average height of the plant itself is 23–25 cm and the average width is 22–25 cm.

Stems:

*Color.*—Young wood: Yellow-Green Group 144A. Older wood: Green Group 137C.

*Prickles.*—Incidence: 10 mm per 10 cm of stem. Size: Average length: 4 mm. Color: On plants grown under high light conditions, peduncle may exhibit intonations of Greyed-Red Group 181D. Shape: Linear.

*Surface.*—Young wood: Smooth. Older wood: Smooth.

Plant foliage: Normal number of leaflets on normal leaves in middle of the stem: 5 leaflets.

*Leaf size.*—95 mm (l)×65 mm (w)

*Quantity.*—Average.

*Color.*—Upper Leaf Surface: Green Group 137A. Lower Leaf Surface: Green Group 138A. Juvenile foliage: Upper Leaf Surface: Yellow-Green Group 144A. Lower Leaf Surface: Green Group 138B. Anthocyanin intonation: None observed.

Plant leaves and leaflets:

*Stipules.*—Size: 15. Color: Yellow-Green Group 144A. Stipitate Glands: On stipule edges.

*Petiole.*—Length: 15 mm to 20 mm. Color: Greyed-Orange Group 166A, with some intonations of Green Group 138B. Underneath: Yellow-Green Group 146B. With a single, small thorn.

*Rachis.*—Color: Greyed-orange Group 166A, with some intonations of Green Group 138B. Underneath: Yellow-Green Group 146B. With a single, small thorn.

*Leaflet.*—Edge: Finely serrated. Shape: Apex is acute; base is round. Glossiness: Moderate. Arrangement: Odd pinnate. Venation: Reticulate. Thickness: Thin.

Disease resistance: Average resistance to mildew, black spot, and Botrytis under normal growing conditions in Half Moon Bay, Calif.

I claim:

1. A new and distinct variety of rose of the miniature class, substantially as herein illustrated and described as a distinct and novel rose variety due to its abundant, pale yellow flowers, vigorous growth, compact habit, suitability for production from softwood cuttings in pots, and durable flowers and foliage which make the variety suitable for distribution in the floral industry.

* * * * *

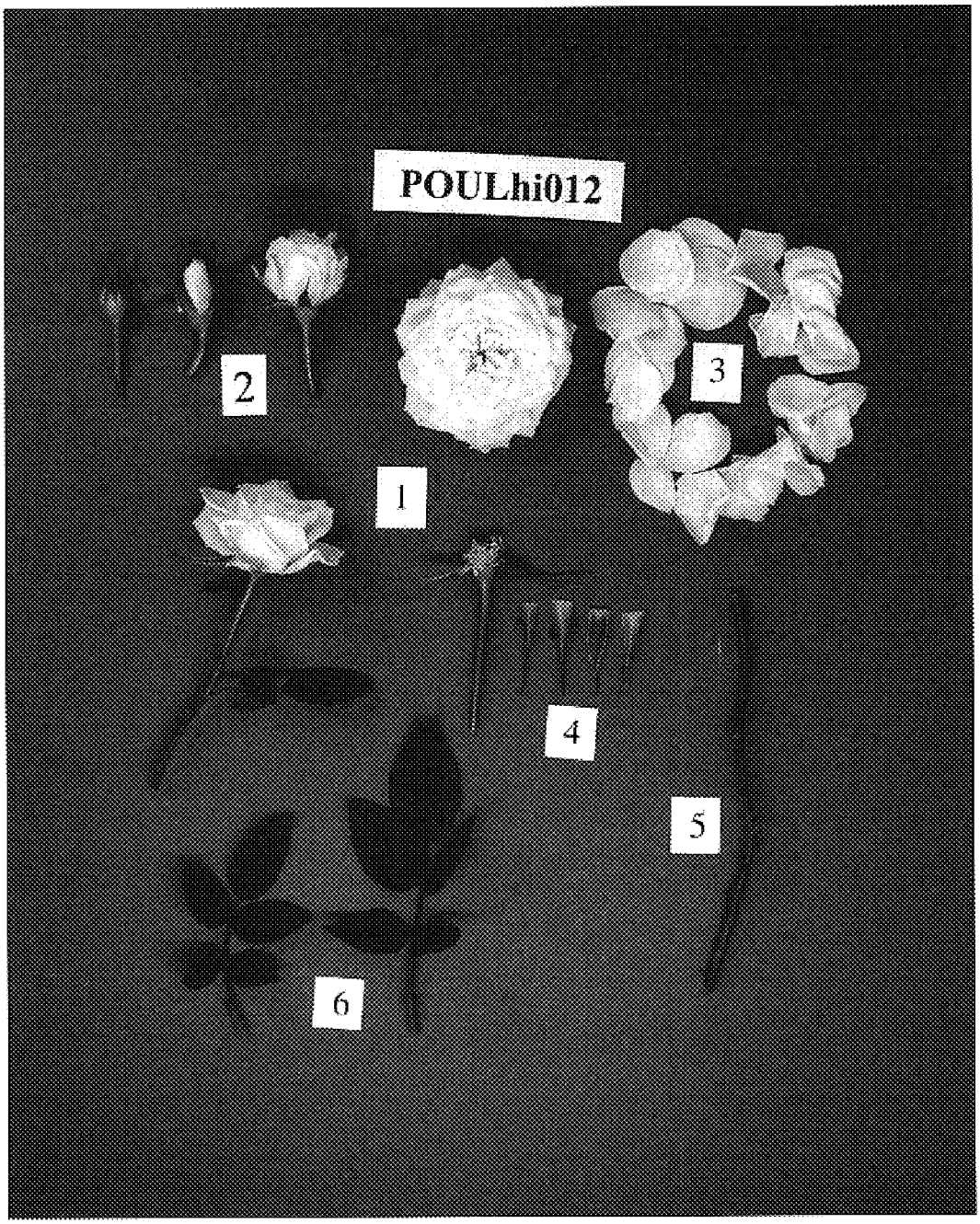
POULhi012
1
2
3
4
5
6